(12) United States Patent
Peng

(10) Patent No.: US 12,286,386 B2
(45) Date of Patent: Apr. 29, 2025

(54) PROCESS TO PRODUCE (Z)-1,1,1,4,4,4-HEXAFLUORO-2-BUTENE AND INTERMEDIATES

(71) Applicant: THE CHEMOURS COMPANY FC, LLC, Wilmington, DE (US)

(72) Inventor: Sheng Peng, Hockessin, DE (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 450 days.

(21) Appl. No.: 17/800,315

(22) PCT Filed: Mar. 3, 2021

(86) PCT No.: PCT/US2021/020628
§ 371 (c)(1),
(2) Date: Aug. 17, 2022

(87) PCT Pub. No.: WO2021/178507
PCT Pub. Date: Sep. 10, 2021

(65) Prior Publication Data
US 2023/0074227 A1    Mar. 9, 2023

Related U.S. Application Data

(60) Provisional application No. 62/985,082, filed on Mar. 4, 2020.

(51) Int. Cl.
*C07C 17/354* (2006.01)
*B01J 23/44* (2006.01)
*C07C 17/20* (2006.01)

(52) U.S. Cl.
CPC ............ *C07C 17/354* (2013.01); *B01J 23/44* (2013.01); *C07C 17/206* (2013.01)

(58) Field of Classification Search
CPC ...... C07C 17/354; C07C 17/206; C07C 17/25; C07C 17/275; C07C 19/10; C07C 21/22; C07C 21/18; B01J 23/44
See application file for complete search history.

(56) References Cited

U.S. PATENT DOCUMENTS

| 6,399,840 B1 | 6/2002 | Schoebrechts |
| 6,500,993 B1 | 12/2002 | Mathieu et al. |
| 8,426,655 B2 | 4/2013 | Tung |
| 8,461,401 B2 | 6/2013 | Tung |
| 11,731,925 B2 * | 8/2023 | Peng ..................... C07C 17/25 570/135 |
| 2012/0119139 A1 | 5/2012 | Baker |

FOREIGN PATENT DOCUMENTS

| CN | 110372473 A | 10/2019 |
| JP | 2000143559 A | 5/2000 |
| JP | 2002505667 A | 2/2002 |
| JP | 2013529216 A | 7/2013 |
| WO | 97/05089 A1 | 2/1997 |
| WO | 2011146820 A2 | 11/2011 |
| WO | 2014/052695 A1 | 4/2014 |
| WO | 2015/120250 A1 | 8/2015 |
| WO | 2015/142981 A1 | 9/2015 |
| WO | 2016/025179 A1 | 2/2016 |
| WO | 2018/022500 A1 | 2/2018 |

* cited by examiner

*Primary Examiner* — Jafar F Parsa

(57) ABSTRACT

A method of producing (Z)-1,1,1,4,4,4-hexafluoro-2-butene (Z-1336mzz) is described. The method utilizes readily available halogenated starting materials, including 1,1,1-trichloro-2,2,2-trifluoroethane (CFC-113a) and carbon tetrachloride.

23 Claims, No Drawings

PROCESS TO PRODUCE (Z)-1,1,1,4,4,4-HEXAFLUORO-2-BUTENE AND INTERMEDIATES

CROSS REFERENCE TO RELATED APPLICATIONS

This application is a national filing under 35 U.S. C. 371 of International Application No. PCT/US2021/020628 filed Mar. 3, 2021, and claims priority of U.S. Provisional Application No. 62/985,082 filed Mar. 4, 2020, the disclosures of which are incorporated herein by reference in its entirety.

FIELD

The present disclosure relates to processes used to produce (Z)-1,1,1,4,4,4-hexafluoro-2-butene (Z-1336mzz) and intermediates useful in such production. In particular, the present disclosure relates to a process for producing (Z)-1,1,1,4,4,4-hexafluoro-2-butene (Z-1336mzz) from readily available halogenated alkanes.

BACKGROUND

The fluorocarbon industry has been working for the past few decades to find replacement refrigerants for the ozone depleting chlorofluorocarbons (CFCs) and hydrochlorofluorocarbons (HCFCs) being phased out as a result of the Montreal Protocol. The solution for many applications has been the commercialization of hydrofluorocarbon (HFC) compounds for use as refrigerants, solvents, fire extinguishing agents, blowing agents and propellants. These new compounds, such as HFC refrigerants, HFC-134a and HFC-125 being the most widely used at this time, have zero ozone depletion potential and thus are not affected by the current regulatory phase-out as a result of the Montreal Protocol.

In addition to ozone depleting concerns, global warming is another environmental concern in many of these applications. Thus, there is a need for compositions that meet both low ozone depletion standards as well as having low global warming potentials (GWPs). Certain hydrofluoroolefin compositions are believed to meet both goals. Thus, there is also a need for economical manufacturing processes that provide these compositions.

(Z)-1,1,1,4,4,4-Hexafluoro-2-butene (Z-1336mzz) is a hydrofluoroolefin having use in refrigerants, heat transfer compositions, thermodynamic cycle (e.g. heating or cooling cycle) working fluids, aerosol propellants, foaming agents (blowing agents), solvents, cleaning agents, carrier fluids, displacement drying agents, buffing abrasion agents, polymerization media, foaming agents for polyolefins and polyurethane, gaseous dielectrics, power cycle working fluids, fire extinguishing agents, and fire suppression agents in liquid or gaseous form. The GWP for cis-HFO-1336mzz has been estimated from atmospheric lifetime to be <10 for the 100 year time horizon.

There is a need in this art for a process that can produce (Z)-1,1,1,4,4,4-hexafluoro-2-butene (Z-1336mzz) efficiently and economically.

SUMMARY

The present disclosure provides processes for the production of hydrofluoroolefin Z-1,1,1,4,4,4-hexafluoro-2-butene (Z—$CF_3CH$=$CHCF_3$, Z-1336mzz) and intermediates useful in its production. The processes set forth herein provide cost-effective synthesis routes to Z-1336mzz starting with $CF_3CCl_3$ and $CH_2$=$CCl_2$ or $CCl_4$ and $CF_3Cl$=$CH_2$.

In an embodiment, a process for producing a product mixture comprising 1,1,1,3,3-pentachloro-4,4,4-trifluorobutane ($CCl_3CH_2CHClCF_3$, 333jfa), comprises contacting a halogenated alkane with an olefin in the presence of a mononitrile and a catalyst comprising copper (II) chloride, wherein the halogenated alkane is chosen from 1,1,1-trichloro-2,2,2-trifluoroethane ($CF_3CCl_3$, 113a) and carbon tetrachloride ($CCl_4$), provided that when the halogenated alkane is 1,1,1-trichloro-2,2,2-trifluoroethane, the olefin is vinylidene chloride ($CH_2$=$CCl_2$, VDC) and when the halogenated alkane is carbon tetrachloride, the olefin is 2-chloro-3,3,3-trifluoropropene ($CF_3CCl$=$CH_2$, 1233xf).

In an embodiment, a process comprises contacting 333jfa, produced as set forth hereinabove, with hydrogen fluoride (HF) in the gas phase or liquid phase, in the presence of a fluorination catalyst under conditions to produce a product mixture comprising 2,2-dichloro-1,1,1,4,4,4-hexafluorobutane ($CF_3CCl_2CH_2CF_3$, 336mfa).

In an embodiment, a process comprises contacting 336mfa, produced as set forth hereinabove, with base, and optionally a phase transfer catalyst, to produce a product mixture comprising 1,1,1,4,4,4-hexafluorobutyne.

In an embodiment, 1,1,1,4,4,4-hexafluoro-2-butyne is reacted with hydrogen and a hydrogenation catalyst to produce a product mixture comprising Z-1,1,1,4,4,4-hexafluoro-2-butene (Z-1336mzz).

The present disclosure provides a process for the production of Z-1,1,1,4,4,4-hexafluoro-2-butene comprising (a) contacting a halogenated alkane with an olefin in the presence of a mononitrile and a catalyst comprising copper (II) chloride, wherein the halogenated alkane is chosen from 1,1,1-trichloro-2,2,2-trifluoroethane and carbon tetrachloride, provided that when the halogenated alkane is 1,1,1-trichloro-2,2,2-trifluoroethane, the olefin is vinylidene chloride and when the halogenated alkane is carbon tetrachloride, the olefin is 2-chloro-3,3,3-trifluoropropene to produce a product mixture comprising 1,1,1,3,3-pentachloro-4,4,4-trifluorobutane; (b) contacting 1,1,1,3,3-pentachloro-4,4,4-trifluorobutane with hydrogen fluoride in the gas phase or liquid phase, in the presence of a fluorination catalyst under conditions to produce a product mixture comprising 2,2-dichloro-1,1,1,4,4,4-hexafluorobutane; (c) contacting 2,2-dichloro-1,1,1,4,4,4-hexafluorobutane with base and a phase transfer catalyst to produce a product mixture comprising 1,1,1,4,4,4-hexafluoro-2-butyne; and (d) contacting 1,1,1,4,4,4-hexafluoro-2-butyne with hydrogen and a hydrogenation catalyst to produce a product mixture comprising Z-1,1,1,4,4,4-hexafluoro-2-butene.

In any of the foregoing processes, the desired product may be recovered from the product mixture comprising such desired product.

The foregoing general description and the following detailed description are exemplary and explanatory only and are not restrictive of the present disclosure, as defined in the appended claims. Other features and advantages of the processes disclosed herein will be apparent from the following more detailed description of the preferred embodiments, taken in conjunction with the present disclosure.

DETAILED DESCRIPTION

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The transitional phrase "consisting of" excludes any element, step, or ingredient not specified. If in the claim, such would close the claim to the inclusion of materials other than those recited except for impurities ordinarily associated therewith. When the phrase "consists of" appears in a clause of the body of a claim, rather than immediately following the preamble, it limits only the element set forth in that clause; other elements are not excluded from the claim as a whole. The transitional phrase "consisting essentially of" is used to define a composition, method that includes materials, steps, features, components, or elements, in addition to those literally disclosed provided that these additional included materials, steps, features, components, or elements do not materially affect the basic and novel characteristic(s), especially the mode of action to achieve the desired result of any of the processes disclosed herein. The term 'consisting essentially of' occupies a middle ground between "comprising" and 'consisting of'.

Also, use of "a" or "an" are employed to describe elements and components described herein. This is done merely for convenience and to give a general sense of the scope of the disclosure. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this disclosure belongs. Although methods and materials similar or equivalent to those described herein can be used in the practice or testing of embodiments of the present disclosure, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

Provided are exemplary synthesis processes of preparing compositions (product mixtures) including (Z)-1,1,1,4,4,4-hexafluoro-2-butene (Z-1336mzz). Embodiments of the present disclosure include synthesis routes to 1,1,1,4,4,4-hexafluoro-2-butene (Z-1336mzz) starting with the readily available halogenated compounds, $CCl_4$, $CF_3CCl_3$, $CH_2=CCl_2$, $CF_3CCl=CH_2$.

The processes disclosed herein may be conducted in a reactor suitable for reaction conditions of temperature and pressure and made of a material that is resistant to the reactants and products employed. The reactor may be constructed from materials which are resistant to the corrosive effects of hydrogen fluoride such as stainless steel, Hastelloy®, Inconel®, Monel®, gold or gold-lined or quartz. The reactions may be conducted batchwise, continuous, semi-continuous or combinations thereof. Suitable reactors include batch reactor vessels and tubular reactors.

By "recover" it is meant to sufficiently isolate the desired product to make it available for its intended use, either as a starting material for a subsequent reaction step or, in the case of recovering Z-1,1,1,4,4,4-hexafluoro-2-butene, useful, for example, as or in a composition as a refrigerant or foam expansion agent or solvent or fire extinguishant or electronic gas or other use.

The details of the recovery step will depend on the compatibility of the product mixture with the reaction conditions of the subsequent reaction step. For example, if the product is produced in a reaction medium that is different from or incompatible with a subsequent reaction step, then the recovery step may include separation of the desired product from the product mixture including the reaction medium. This separation may occur simultaneously with the contacting step when the desired product is volatile under the reaction conditions. The volatilization of the desired product can constitute the isolation and thereby the recovery of the desired product. If the volatilized product includes undesired components, the desired product may be separated, by selective distillation, for example.

The steps for recovering the desired product from the product mixture, preferably comprise separating the desired product from catalyst or other component(s) of the product mixture used to produce the desired product or produced in the process.

The present disclosure provides, inter alia, processes to produce Z-1336mzz, and intermediates for producing Z-1336mzz. Such process uses low cost, readily available starting materials such as 1,1,1-trichloro-2,2,2-trifluoroethane and carbon tetrachloride.

Production of 1,1,1,3,3-pentachloro-4,4,4-trifluorobutane ($CCl_3CH_2CHClCF_3$, 333jfa)

In an embodiment for producing 1,1,1,3,3-pentachloro-4,4,4-trifluorobutane ($CF_3CCl_2CH_2CCl_3$, 333jfa), 1,1,1-trichloro-2,2,2-trifluoroethane ($CF_3CCl_3$, 113a) is charged to a reactor, heated, and contacted with vinylidene chloride ($CH_2=CCl_2$, VDC), in the presence of a catalyst comprising copper (II) chloride and a mononitrile, at a temperature and pressure sufficient to form 1,1,1,3,3-pentachloro-4,4,4-trifluorobutane, as shown in Scheme (1A).

Scheme 1A

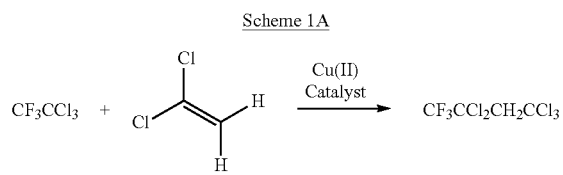

In an alternate embodiment for producing 1,1,1,3,3-pentachloro-4,4,4-trifluorobutane, carbon tetrachloride ($CCl_4$) is charged to a reactor, heated, and contacted with 2-chloro-3,3,3-trifluoropropene ($CF_3CCl=CH_2$, 1233xf), in the presence of a catalyst comprising copper (II) chloride and a mononitrile, at a temperature and pressure sufficient to form 1,1,1,3,3-pentachloro-4,4,4-trifluorobutane, as shown in Scheme (1B).

Scheme 1B

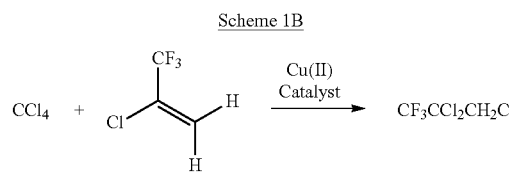

In some embodiments, the above additions of a halogenated alkane to an olefin may be performed at a temperature of about 50° C. to about 150° C. In some embodiments the temperature is 50 to 130° C. In some embodiments, the reaction is performed as a batch reaction and reaction time may be up to 2 hours, up to 5 hours, up to 10 hours, up to 15 hours, up to 18 hours, up to 20 hours, up to 22 hours, up to 24 hours, less than 36 hours, less than 32 hours, less than 28 hours, less than 26 hours, and combinations thereof.

In some embodiments, the reaction may be performed at a reactor pressure of 1 pound per square inch gauge (psig) to 300 pounds per square inch gauge (psig) (about 7 to about 2000 kPa).

The mononitrile may be chosen from acetonitrile, propionitrile, butyronitrile. In some embodiments, the mononitrile is propionitrile. The molar ratio of mononitrile to the Cu(II) catalyst is at least 10 and no more than 25. This ratio may be between 10 and 20 or between 15 and 25 or between 15 and 20.

The process to produce 333jfa may further comprise recovering 333jfa from the product mixture prior to use of the recovered 333jfa as a starting material in a process to produce HCFC-336mfa, 1,1,1,4,4,4-hexafluoro-2-butyne and HFO—Z-1336mzz, for example, as set forth herein. Processes for recovering 333jfa from the product mixture may include one or any combination of purification techniques, such as distillation, that are known in the art. By "recovering" 333jfa from the product mixture, a product comprising at least 95% or at least 97% or at least 99% 333jfa is produced.

Production of 2,2-dichloro-1,1,1,4,4,4-hexafluorobutane ($CF_3CCl_2CH_2CF_3$, 336mfa)

In an embodiment, 1,1,1,3,3-pentachloro-4,4,4-trifluorobutane (333jfa) undergoes a fluorination reaction. In this embodiment, 1,1,1,3,3-pentachloro-4,4,4-trifluorobutane is contacted with hydrogen fluoride (HF) in the presence of a fluorination catalyst at a temperature and pressure sufficient to form a product comprising 2,2-dichloro-1,1,1,4,4,4-hexafluorobutane, as shown in Scheme (2).

Scheme 2

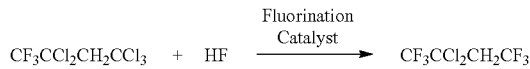

The reaction with HF may be carried out in the gas phase or the liquid phase. A liquid medium may be added to the liquid phase reaction. An example of a liquid medium is the 333jfa reactant itself. The gas phase or liquid phase reaction includes a fluorination catalyst.

The fluorination reaction may be conducted in a reaction zone comprising any reaction vessel of appropriate size for the scale for the reaction. In some embodiments, the reaction zone comprises a reaction vessel comprised of materials which are resistant to corrosion. In some embodiments, these materials comprise alloys, such as nickel-based alloys such as Hastelloy®, nickel-chromium alloys commercially available from Special Metals Corp. under the trademark Inconel® (hereinafter "Inconel®") or nickel-copper alloys commercially available from Special Metals Corp. (New Hartford, New York) under the trademark Monel®, or vessels having fluoropolymers linings. In other embodiments, the reaction vessel may be made of other materials of construction including stainless steels, in particular of the austenitic type, and copper-clad steel.

In a catalyzed gas phase fluorination process, the fluorination catalyst may be chosen from carbon; graphite; alumina; fluorinated alumina; aluminum fluoride; alumina supported on carbon; aluminum fluoride supported on carbon; fluorinated alumina supported on carbon; magnesium fluoride supported on aluminum fluoride; metals (including elemental metals, metal oxides, metal halides, and/or other metal salts); metals supported on aluminum fluoride; metals supported on fluorinated alumina; metals supported on alumina; and metals supported on carbon; mixtures of metals.

Suitable metals for use in gas phase fluorination catalysts (optionally supported on alumina, aluminum fluoride, fluorinated alumina, or carbon) include chromium, iron, cobalt, nickel, ruthenium, rhodium, palladium, osmium, iridium, platinum, manganese, rhenium, scandium, yttrium, lanthanum, titanium, zirconium, and hafnium, copper, silver, gold, zinc, and/or metals having an atomic number of 58 through 71 (i.e., the lanthanide metals). Preferably when used on a support, the total metal content of the catalyst will be from about 0.1 to about 20 percent by weight based on the total weight of the catalyst; typically from about 0.1 to about 10 percent by weight based on the total weight of the catalyst.

Useful fluorination catalysts for the gas phase process include chromium-based catalysts, such as chromium oxyfluoride or chromium oxide, which catalyst may either be unsupported, or supported on a support such as activated carbon, graphite, fluorinated graphite, or fluorinated alumina. The chromium catalyst may either be used alone, or in the presence of a co-catalyst selected from nickel, cobalt, manganese or zinc salt. In some embodiments, a chromium catalyst is high surface area chromium oxide, or chromium/nickel on fluoride alumina ($Cr/Ni/AlF_3$), the production of which is reported in European Patent EP 486,333.

Chromium oxyfluoride catalysts may be made by processes known to those skilled in the art, such as, for example by treating $Cr_2O_3$ (chromium oxide) with HF, $CCl_3F$ or hydrofluorocarbons, as disclosed in WO 2012/067864 A1.

Chromium catalysts are preferably activated before use, for example, as disclosed in U.S. Pat. No. 9,302,962.

In a gas phase fluorination process, the molar ratio of HF to 333jfa in some embodiments may be from about 1 to about 35. In other embodiments, the molar ratio of HF to 333jfa is from about 1 to about 25. HF may be added in an amount of 10 to 30 moles per mole of 333jfa.

In some embodiments, the gas phase fluorination process is performed at an elevated temperature, for example at a temperature in the range of 150 to 400° C. or from 275 to 375° C. In some embodiments, the temperature is in the range of 300 to 350° C.

In some embodiments, the gas phase fluorination process is performed at a pressure in the range of 0 to 200 psi (0 to 1.4 MPa). In some embodiments, the reaction is performed at substantially atmospheric pressure.

In some embodiments, contact time for the gas phase fluorination process may be from about 1 second to about 100 seconds. In some embodiments, contact time for the gas phase fluorination process may be from about 10 to about 100 seconds or 10 seconds to 30 seconds. In other embodiments, contact time for the gas phase fluorination process may be from 50 to about 80 seconds.

The gas phase fluorination reaction may further comprise recovering 336mfa from the product mixture to reduce the other components of the product mixture. Processes for recovering 336mfa may include one or any combination of purification techniques, such as distillation, that are known in the art. By "recovering" 336mfa from the product mixture, a product comprising at least 98.5% or at least 99 or at least 99.5% 336mfa is produced.

In a catalyzed liquid phase fluorination process, the fluorination catalyst may include Lewis acid catalyst such as metal halides. The halide may be chosen from fluoride, chloride, bromide. The metal halide may be a transition metal halide or other metal halide. Transition metal chlorides include halides of titanium, tantalum, niobium, tin, tungsten and antimony. Other suitable metal halide catalysts include boron trifluoride.

In some embodiments, the fluorination catalyst is chosen from $SbF_5$, $SbCl_5$, $SbCl_3$, $SnCl_4$, $TaCl_5$, $TiCl_4$, $NbCl_5$, $MoCl_6$, $WCl_6$, antimony (V) chlorofluorides, and combinations thereof. In some embodiments, the metal halide is $SbF_5$. In some embodiments, the metal halide is $TaCl_5$. In some embodiments, the metal halide is antimony (V) chlorofluorides. In one embodiment, the catalyst includes tantalum pentachloride, antimony pentachloride, or antimony pentafluoride.

In a liquid phase fluorination process, the hydrogen fluoride is present at a molar ratio of HF to 333jfa of between 7:1 to 15:1. In one embodiment, the hydrogen fluoride is present at a molar ratio of HF to 333jfa of about 10:1.

In some embodiments, the liquid phase fluorination process is performed at a temperature of between 50° C. and 160° C. In some embodiments, the temperature may be greater than 100° C. In other embodiments, the temperature may be less than 150° C.

In some embodiments, the liquid phase fluorination reaction is performed at a pressure in the range of 0 to 600 psi (0 to 4.1 MPa). In some embodiments, the reaction is performed at substantially atmospheric pressure.

In some embodiments, the contact time of a liquid phase fluorination reaction is from about 1 minute to about 24 hours or from about 10 minutes to about 12 hours or from about 1 hour to about 6 hours.

The desired product HCFC-336mfa may be recovered from the reactor when the process is carried out in a liquid medium by purging unreacted chlorine, distilling off unreacted 333jfa, and filtering off the catalyst. When performed in the liquid phase, the catalyst may be filtered off if present in sufficiently high concentration that catalyst precipitates from product mixture prior to or during or after distillation. Alternatively, the catalyst may remain in the distillation heel.

In some embodiments, the product mixture from the fluorination reaction may undergo recovery and purification steps. Such steps may include washing with water, drying, and distillation.

The product produced in a gas phase or liquid phase fluorination process may comprise $CF_3CCl_2CH_2CF_3$ (336mfa) and additional compounds chosen from $CF_3CCl_2CH_2CFCl_2$, $CHF_2CH_2CCl_2CF_3$ and mixtures thereof.

Production of 1,1,1,4,4,4-hexafluoro-2-butyne

The present disclosure further provides a process comprising contacting HCFC-336mfa with base to produce a product mixture comprising 1,1,1,4,4,4-hexafluoro-2-butyne ($CF_3C{\equiv}CCF_3$) in a dehydrochlorination reaction, as shown in Scheme (3). The base is preferably a basic aqueous medium. This reaction step is preferably performed in the presence of a phase transfer catalyst.

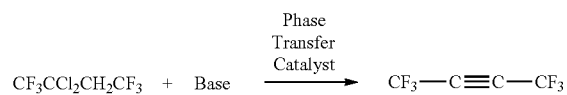

Scheme 3

$$CF_3CCl_2CH_2CF_3 + Base \xrightarrow{\text{Phase Transfer Catalyst}} CF_3{-}C{\equiv}C{-}CF_3$$

The base is a basic aqueous medium comprising a solution of an alkali metal hydroxide or alkali metal halide salt or other base in water. The base may be chosen from hydroxide, oxide, carbonate, or phosphate salts of alkali, alkaline earth metals and mixtures thereof. In some embodiments, the base is chosen from lithium hydroxide, sodium hydroxide, potassium hydroxide, calcium hydroxide, magnesium oxide, calcium oxide, sodium carbonate, potassium carbonate, sodium phosphate, potassium phosphate, and mixtures thereof.

In some embodiments the basic aqueous solution has a pH of over 8. In some embodiments, the basic aqueous solution has a pH of over 10. In some embodiments, the basic aqueous solution has a pH of 10-13. In some embodiments, the basic aqueous solution contains small amounts of organic liquids which may be miscible or immiscible with water. In some embodiments, the liquid in the basic aqueous solution is at least 90% water. In some embodiments the water is tap water; in other embodiments the water is deionized or distilled.

This reaction step is preferably performed in the presence of a phase transfer catalyst. As used herein, phase transfer catalyst is intended to mean a substance that facilitates the transfer of ionic compounds into an organic phase from an aqueous phase. In this step, the organic phase comprises the HCFC-336mfa reactant, and the aqueous phase comprises the basic aqueous medium. The phase transfer catalyst facilitates the reaction of these dissimilar and incompatible components. While various phase transfer catalysts may function in different ways, their mechanism of action is not determinative of their utility in processes of the present disclosure provided, that the phase transfer catalyst facilitates the dehydrochlorination reaction.

Suitable phase transfer catalysts include quaternary alkylammonium salts. In some embodiments, the catalyst includes tetrabutylammonium bromide or N-methyl-N,N,N-trioctylammonium chloride. In some embodiments, at least one alkyl group of the quaternary alkylammonium salt contains at least 8 carbons. An example of quaternary alkylammonium salt wherein three alkyl groups contain at least 8 carbon atoms is N-methyl-N,N,N-trioctylammonium chloride, sold under the tradename ALIQUAT® 336, by Alfa Aesar-Fisher Scientific. An example of quaternary alkylammonium salt wherein four alkyl groups contain at least 8 carbon atoms includes tetraoctylammonium salt.

The anions of such salts may be halides such as chloride or bromide, hydrogen sulfate, or any other commonly used anion.

Specific quaternary alkylammonium salts include tetraoctylammonium chloride, tetraoctylammonium hydrogen sulfate, tetraoctylammonium bromide, methytrioctylammonium chloride, methyltrioctylammonium bromide, tetradecylammonium chloride, tetradecylammonium bromide, and tetradodecylammonium chloride.

According to one embodiment, a process to produce a product mixture comprising $CF_3C{\equiv}CCF_3$ comprises contacting 336mfa with base and a phase transfer catalyst under reaction conditions effective to achieve conversion of 336mfa of at least 50% per hour.

In other embodiments, the alkyl groups of the quaternary alkylammonium salt contain from 4 to 10 carbon atoms and a non-ionic surfactant is present in the aqueous basic medium. According to such embodiments, the phase transfer catalyst and reaction conditions are effective to achieve conversion of HCFC-336mfa preferably at least 20% per hour. The anions of quaternary alkylammonium salt wherein the alkyl group contains 4 to 10 carbon atoms may be halides such as chloride or bromide, hydrogen sulfate, or any other commonly used anion. Quaternary alkylammonium salts mentioned above may be used in this embodiment provided their alkyl groups contain 4 to 10 carbon atoms. Specific additional salts include tetrabutylammonium chloride, tetrabutylammonium bromide, and tetrabutylammonium hydrogen sulfate.

Preferred non-ionic surfactants include ethoxylated nonylphenol or an ethoxylated C12-C15 linear aliphatic alcohol. Useful non-ionic surfactants include Bio-soft® N25-9 and Makon® 10, which are obtainable from Stepan Company, Northfield, IL In some embodiments, the quaternary alkylammonium salt is added in an amount of from 0.5 mole percent to 2 mole percent of the HCFC-336mfa. In other embodiments, the quaternary alkylammonium salt is added in an amount of from 1 mole percent to 2 mole percent of the HCFC-336mfa. In yet other embodiments, the quaternary alkylammonium salts is added in an amount of from 1 mole percent to 1.5 mole percent of the HCFC-336mfa. In some embodiments, the quaternary alkylammonium salt is added in an amount of from 1 mole percent to 1.5 mole percent of the HCFC-336mfa and the weight of non-ionic surfactant added is from 1 to 2 times the weight of the quaternary alkylammonium salt. These amounts apply to each of the above-mentioned embodiments of the quaternary alkylammonium salt used.

In some embodiments, the reaction mixture is heated to a temperature of 50° C. to 95° C., preferably conducted at a temperature of from about 60 to 90° C., most preferably at 70° C.

In some embodiments, the reaction is heated for about 1 hour to about 10 hours, about 2 hours to about 6 hours, about 4 hours to about 5 hours, and combinations thereof.

In some embodiments, the reaction is performed at substantially atmospheric pressure.

In some embodiments, the base includes a strong base. In some embodiments, the base includes sodium hydroxide or potassium hydroxide.

In some embodiments, the dehydrochlorination reaction of 336mfa to 1,1,1,4,4,4-hexafluoro-2-butyne is performed in the presence of an alkali metal halide salt. The alkali metal may be sodium or potassium. The halide may be chloride or bromide. A preferred alkali metal halide salt is sodium chloride. Without wishing to be bound by any particular theory, it is believed that the alkali metal halide salt stabilizes the phase transfer catalyst. Although the dehydrochlorination reaction itself produces alkali metal chloride, and in particular sodium chloride if sodium hydroxide is used as the base, addition of extra sodium chloride provides a further effect of increasing the yield of 1,1,1,4,4,4-hexafluoro-2-butyne. In some embodiments, the alkali metal halide is added at from about 25 to about 100 equivalents per mole of phase transfer catalyst. In other embodiments, the alkali metal halide is added at from about 30 to about 75 equivalents per mole of phase transfer catalyst. In yet other embodiments, the alkali metal halide is added at from about 40 to about 60 equivalents per mole of phase transfer catalyst. These amounts apply to each of the quaternary alkylammonium salts mentioned above.

The product 1,1,1,4,4,4,-hexafluoro-2-butyne (boiling point −25° C.) may be recovered from the product mixture by distillation, wherein the butyne vaporizes from the aqueous medium and can then be condensed.

Production of Z-1,1,1,4,4,4-hexafluoro-2-butene

The present disclosure further provides a hydrogenation process comprising contacting 1,1,1,4,4,4-hexafluoro-2-butyne with hydrogen at a temperature and pressure sufficient to produce a product mixture comprising Z-1,1,1,4,4,4-hexafluoro-2-butene (Z-1336mzz), as shown in Scheme (4). This process is preferably performed in the presence of a hydrogenation catalyst, which is an alkyne-to-alkene catalyst.

Scheme 4

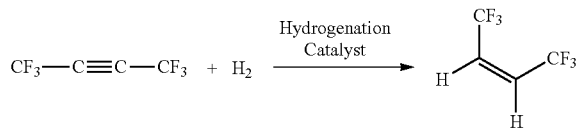

In some embodiments, the hydrogenation catalyst is a palladium catalyst, such as a catalyst comprising palladium dispersed on aluminum oxide or titanium silicate, doped with silver and/or a lanthanide. The loading of palladium dispersed on the aluminum oxide or titanium silicate is relatively low. In some embodiments, the palladium loading is from about 100 ppm to about 5000 ppm. In other embodiments, the palladium loading is from about 200 ppm to about 5000 ppm. In some embodiments, the palladium catalyst is doped with at least one of silver, cerium or lanthanum. In some embodiments, the mole ratio of cerium or lanthanum to palladium is from about 2:1 to about 3:1. In some embodiments the mole ratio of silver to palladium is about 0.5:1.0.

In some embodiments, the hydrogenation catalyst includes Lindlar (5% Pd on $CaCO_3$ poisoned with lead). The lead compound may be lead acetate, lead oxide, or any other suitable lead compound.

The Lindlar catalyst may be further deactivated or conditioned with quinoline. The amount of palladium on the support is typically about 5% by weight but may be any catalytically effective amount. In some embodiments, the amount of palladium on the support in the Lindlar catalyst is greater than 5% by weight. In yet other embodiments, the amount of palladium on the support may be from about 5% by weight to about 1% by weight.

In some embodiments, the amount of the catalyst used is from about 0.5% by weight to about 4% by weight of the amount of the 1,1,1,4,4,4-hexafluoro-2-butyne. In other embodiments, the amount of the catalyst used is from about 1% by weight to about 3% by weight of the amount of the butyne. In yet other embodiments, the amount of the catalyst used is from about 1% to about 2% by weight of the amount of the butyne.

In some embodiments, the amount of the catalyst used is from about 0.5% by weight to about 4% by weight of the amount of the 1,1,1,4,4,4-hexafluoro-2-butyne. In other embodiments, the amount of the catalyst used is from about 1% by weight to about 3% by weight of the amount of the butyne. In yet other embodiments, the amount of the catalyst used is from about 1% to about 2% by weight of the amount of the butyne.

In some embodiments, this reaction step is performed in the presence of a solvent. In one such embodiment, the solvent is an alcohol. Typical alcohol solvents include ethanol, i-propanol and n-propanol. In other embodiments, the solvent is a fluorocarbon or hydrofluorocarbon. Typical fluorocarbons or hydrofluorocarbons include 1,1,1,2,2,3,4,5,5,5-decafluoropentane and 1,1,2,2,3,3,4-heptafluorocyclopentane.

In some embodiments, reaction of the 1,1,1,4,4,4-hexafluoro-2-butyne with hydrogen is preferably performed with addition of hydrogen in portions, with increases in the pressure of the vessel of no more than about 100 psi (0.69 MPa) with each addition. In other embodiments, the addition of hydrogen is controlled so that the pressure in the vessel increases no more than about 50 psi (0.35 MPa) with each addition. In some embodiments, after enough hydrogen has been consumed in the hydrogenation reaction to convert at least 50% of the butyne to Z-1336mzz, hydrogen may be added in larger increments for the remainder of the reaction. In other embodiments, after enough hydrogen has been consumed in the hydrogenation reaction to convert at least 60% of the butyne to the desired butene, hydrogen may be added in larger increments for the remainder of the reaction. In yet other embodiments, after enough hydrogen has been consumed in the hydrogenation reaction to convert at least 70% of the butyne to desired butene, hydrogen may be added in larger increments for the remainder of the reaction. In some embodiments, the larger increments of hydrogen addition may be 300 psi (2.07 MPa). In other embodiments, the larger increments of hydrogen addition may be 400 psi (2.76 MPa).

In some embodiments, the molar ratio is about 1 mole of hydrogen to about 1 mole of 1,1,1,4,4,4-hexafluoro-2-butyne. In other embodiments, the molar ratio is from about 0.9 mole to about 1.3 mole, hydrogen to butyne. In yet other embodiments, the amount of hydrogen added is from about 0.95 mole of hydrogen to about 1.1 moles of butyne. In yet other embodiments, the amount of hydrogen added is from about 0.95 moles of hydrogen to about 1.03 moles of butyne.

In some embodiments, the hydrogenation is performed at ambient temperature (15° C. to 25° C.). In other embodiments, the hydrogenation is performed at above ambient temperature. In yet other embodiments, the hydrogenation is performed at below ambient temperature. In yet other embodiments, the hydrogenation is performed at a temperature of below about 0° C.

In some embodiments, a reaction vessel containing hexafluoro-2-butyne and catalyst is cooled to about −78° C. under reduced pressure. The temperature of the reactor may then be allowed to warm to room temperature. Hydrogen gas may then be slowly added to the reaction vessel. In some embodiments, the rate of addition of hydrogen gas is regulated to result in a pressure change within the reaction vessel of less than 70 psi, less than 60 psi, and/or less than 50 psi. The addition of hydrogen may be continued until a slight excess of hydrogen is provided to the reaction vessel.

In an embodiment of a continuous process, a mixture of 1,1,1,4,4,4-hexafluoro-2-butyne and hydrogen is passed through a reaction zone containing the catalyst. A reaction vessel, e.g., a metal tube, may be used, packed with the catalyst to form the reaction zone. In some embodiments, the molar ratio of hydrogen to the butyne is about 1:1. In other embodiments of a continuous process, the molar ratio of hydrogen to the butyne is less than 1:1. In yet other embodiments, the molar ratio of hydrogen to the butyne is about 0.67:1.0.

In some embodiments of a continuous process, the reaction zone is maintained at ambient temperature. In other embodiments of a continuous process, the reaction zone is maintained at a temperature of 30° C. In yet other embodiments of a continuous process, the reaction zone is maintained at a temperature of about 40° C.

In some embodiments of a continuous process, the flow rate of 1,1,1,4,4,4-hexafluoro-2-butyne and hydrogen is maintained so as to provide a residence time in the reaction zone of about 30 seconds. In other embodiments of a continuous process, the flow rate of the butyne and hydrogen is maintained so as to provide a residence time in the reaction zone of about 15 seconds. In yet other embodiments of a continuous process, the flow rate of butyne and hydrogen is maintained so as to provide a residence time in the reaction zone of about 7 seconds.

It will be understood, that contact time in the reaction zone is reduced by increasing the flow rate of 1,1,1,4,4,4-hexafluoro-2-butyne and hydrogen into the reaction zone. As the flow rate is increased this will increase the amount of butyne being hydrogenated per unit time. Since the hydrogenation is exothermic, depending on the length and diameter of the reaction zone, and its ability to dissipate heat, at higher flow rates it may be desirable to provide a source of external cooling to the reaction zone to maintain a desired temperature.

In some embodiments, upon completion of a batch-wise or continuous hydrogenation process, the Z-1336mzz may be recovered through any conventional process, including for example, fractional distillation. In other embodiments, upon completion of a batch-wise or continuous hydrogenation process, the Z-1336mzz is of sufficient purity to not require further purification steps.

The 1,1,1,4,4,4-hexafluoro-2-butene reaction product may be recovered in high yield and high purity by distillation of the reaction mixture. In some embodiments, the yield of the reaction of Scheme 4 is greater than 95 percent, greater than 96 percent, greater than 97 percent, and/or greater than 98 percent.

EXAMPLES

The concepts described herein will be further described in the following examples, which do not limit the scope of the present disclosure as described in the claims.

Iron powder, vinylidene chloride, Aliquat® 336 and sodium hydroxide are available from Sigma Aldrich, St. Louis, MO.

113a 1,1,1-trichloro-2,2,2-trifluoroethane ($CF_3CCl_3$), 2-chloro-3,3,3-trifluoropropene ($CF_3CCl=CH_2$), hydrogen fluoride and $SbCl_5$ are purchased from Synquest Labs, Inc.

Example 1 (Comparison). Step 1. VDC Insertion of 113a to Produce $CF_3CCl_2CH_2CCl_3$ Vinylidene chloride (26 g, 0.265 mol) was added to the mixture of 113a (100 g, 0.53 mol), Fe powder (0.62 g, 0.011 mol) and triphenyl phosphine (1.41 g, 0.0054 mol) in a 240 mL Hastelloy reactor. The reactor was heated up to 150° C. for 5 hours. The mixture was transferred to a container and analyzed by GC: 24% GC yield (conversion 30% and selectivity to product 80%).

Example 2. Step 1. VDC Insertion of 113a to Produce $CF_3CCl_2CH_2CCl_3$

The mixture of Vinylidene chloride (2.4 g, 0.025 mol) and 113a (23 g, 0.125 mol) was heated up to 100° C. for 24 hours in the presence of anhydrous copper (II) chloride (0.34 g, 0.0025 mol) along with 3 mL of propionitrile in a 100 mL stainless autoclave. The mixture was transferred to a container and analyzed by GC: 32% GC yield (conversion 40%, selectivity to product 80%).

Example 3 (Comparison). Step 1. 2-chloro-3,3,3-trifluoropropene Insertion of CCl$_{14}$ to Produce CF$_3$CCl$_2$CH$_2$CCl$_3$ The mixture of 2-chloro-3,3,3-trifluoropropene (32.6 g, 0.25 mol) and CCl4 (77 g, 0.5 mol) was heated up to 130° C. for 5 hours in the presence of Fe powder (0.62 g, 0.011 mol) and triphenyl phosphine (1.40 g, 0.005 mol) in a 300 mL Hastelloy reactor. The mixture was transferred to a container and analyzed by GC: conversion 55% and selectivity to product is 86%.

Example 4. Step 1. 2-chloro-3,3,3-trifluoropropene Insertion of CCl$_4$ to Produce CF$_3$CCl$_2$CH$_2$CCl$_3$ The mixture of 2-chloro-3,3,3-trifluoropropene (3.3 g, 0.025 mol) and CCl4 (7.7 g, 0.05 mol) was heated up to 100° C. for 22 hours in the presence of anhydrous copper (II) chloride (0.34 g, 0.0025 mol) in 3 mL of propionitrile in a 100 mL stainless autoclave. The mixture was purified by fractionation and the distilled yield to the product is 62%.

The product CF3CCl2CH2CCl3 was recovered from the product mixtures of Examples 1-4 and has the following properties: boiling point of 56-58° C. (13 mm Hg); 1H NMR (CDCl3): δ ppm 3.72 (CH2, s); 19F NMR (CDCl3): δ ppm −80.47 (CF3, s); MS (m/z): 248.75 (M+−Cl), 246.75 (M+−Cl-2H).

Example 5. Step 2: Liquid Phase Fluorination of CF3CCl2CH2CCl3 to Produce CF3CCl2CH2CF3 (336mfa) Using Antimony Catalyst A mixture of 1,1,1,3,3-pentachloro-4,4,4-trifluorobutane (2 g, 0.007 mol), anhydrous HF (4.2 g, 0.021 mol) and antimony pentachloride (0.5 g, 0.002 mol) was stirred in a PTFE-lined vessel at 110° C. The reaction mixture was poured into crushed ice. The organic layer was washed with water (two times), dried with MgSO4. Distillation at 65-68° C. gave 1.9 g product (81% yield). The product was recovered having the following properties: 1H NMR (CDCl3): δ ppm 3.15 (q, JHF=9.4 Hz, CH2); 19F NMR (CDCl3): δ ppm: −62.7 (t, JFH=9.4 Hz, 2F, CH2CF3), −83.2 (s, 3F, CF3).

Example 6. Step 2: Liquid Phase Fluorination of CF3CCl2CH2CCl3 to Produce CF3CCl2CH2CF3 (336mfa) Using Tantalum Catalyst The mixture of 1,1,1,3,3-pentachloro-4,4,4-trifluorobutane (2 g, 0.007 mol), anhydrous HF (4.2 g, 0.021 mol) and tantalum pentachloride (0.6 g, 0.002 mol) is stirred at in a PTFE-lined vessel at 130° C. The reaction mixture is poured into crushed ice. The organic layer is washed with water (two times), dried with MgSO4. Distillation at 65-68° C. gives 2.1 g product (88% yield).

Example 7. Step 2: Gas phase fluorination of CF3CCl2CH2CCl3 to Produce CF3CCl2CH2CF3 (336mfa)

An Inconel® pipe (0.5 inch OD, 10 inch length, 0.034 in wall thickness) is filled with 6 cc Newport chrome catalyst. The reactor is heated to the target temperature. CF3CCl2CH2CCl3 is fed via an ISCO pump (4.27 mL/hr) and a vaporizer controlled at 170° C. HF/CF3CCl2CH2CCl3 mole ratio is 10 and contact time is 10 seconds. The reaction is run at 0 psig. The reactor effluent is analyzed online using an Agilent® 6890 GC/5973 MS to show 95% conversion of the starting material, 70% selectivity to 336mfa and 30% selectivity to 1326mxz (CF3CCl═CHCF3).

Example 8. Step 3. Conversion of CF3CCl2CH2CF3 to hexafluoro-2-butyne Using Aliquat® 336 Quaternary Ammonium Salt NaOH aqueous solution (22 mL, 0.22 mol) is added to CF3CCl2CH2CF3 (23.5 g, 0.1 mol) and water (5.6 mL) in the presence of Aliquat® 336 quaternary ammonium salt (0.53 g, 0.001325 mol) at room temperature. The reaction temperature is raised to 70° C. after the addition, and gas chromatography is used to monitor the reaction. The reaction is completed after 2 hours and the hexafluorobutyne is collected in a dry ice trap in greater than 90% yield.

Example 9. Step 3. Conversion of CF3CCl2CH2CF3 to hexafluoro-2-butyne Using Tetrabutylammonium Bromide and Surfactant NaOH aqueous solution (22 mL, 0.22 mol) is added to the 336mfa (23.5 g, 0.1 mol) and water (5.6 mL) in the presence of tetrabutylammonium bromide (0.45 g, 0.001325 mol) and Makon® 10 surfactant (0.7 g) at room temperature. The reaction temperature is raised to 70° C. after the addition, and gas chromatography is used to monitor the reaction. The reaction is completed after 4.5 hours and the hexafluorobutyne is collected in a dry ice trap in greater than 90% yield.

Example 10. Step 4. Conversion of 1,1,1,4,4,4-hexafluorobutyne to (Z)-1,1,1,4,4,4-hexafluoro-2-butene 5 g of Lindlar (5% Pd on CaCO3 poisoned with lead) catalyst was charged in a 1.3 L rocker bomb. 480 g (2.96 mol) of hexafluoro-2-butyne was charged in the rocker. The reactor was cooled to −78° C. and evacuated. After the bomb was warmed to room temperature, H2 was added slowly, by increments which did not exceed ΔP=50 psi (0.35 MPa). A total of 3 moles H2 were added to the reactor. A gas chromatographic analysis of the crude product indicated the mixture consisted of CF3C≡CCF3 (0.236%), trans-isomer (E)-CF3CH═CHCF3 (boiling point 33.3° C., MS: 164 [MI], 145 [M-19], 95 [CF3CH═CH], 69 [CF3]; 1H NMR: 6.12 ppm (multiplet), 19F NMR: −60.9 ppm (triplet J=0.86 Hz). The selectivity of this reaction to the formation of the Z-isomer was 96.98%. The Z-isomer was recovered by distillation.

Note that not all of the activities described above in the general description or the examples are required, that a portion of a specific activity may not be required, and that one or more further activities may be performed in addition to those described. Still further, the order in which activities are listed are not necessarily the order in which they are performed.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

While the processes as disclosed herein have been described with reference to a preferred embodiment, it will be understood by those skilled in the art that various changes may be made and equivalents may be substituted for elements thereof without departing from the scope of this disclosure. In addition, many modifications may be made to adapt a particular situation or material to the teachings of the disclosure without departing from the essential scope thereof.

What is claimed is:

1. A process for producing a product mixture comprising 1,1,1,3,3-pentachloro-4,4,4-trifluorobutane ($CCl_3CH_2CCl_2CF_3$, 333jfa), comprises contacting a halogenated alkane with an olefin in the presence of a mononitrile and a catalyst comprising copper (II) chloride, wherein the halogenated alkane is chosen from 1,1,1-trichloro-2,2,2-trifluoroethane ($CF_3CCl_3$, 113a) and carbon tetrachloride ($CCl_4$), provided that when the halogenated alkane is 1,1,1-trichloro-2,2,2-trifluoroethane, the olefin is vinylidene chloride ($CH_2=CCl_2$, VDC) and when the halogenated alkane is carbon tetrachloride, the olefin is 2-chloro-3,3,3-trifluoropropene ($CF_3CCl=CH_2$, 1233xf).

2. The process of claim 1 wherein the mononitrile is chosen from acetonitrile, propionitrile, butyronitrile.

3. The process of claim 2 wherein the mononitrile is propionitrile.

4. The process of claim 1 wherein the halogenated alkane is 1,1,1-trichloro-2,2,2-trifluoroethane and the olefin is vinylidene chloride.

5. The process of claim 1 wherein the halogenated alkane is carbon tetrachloride and the olefin is 2-chloro-3,3,3-trifluoropropene.

6. The process of claim 1 wherein the molar ratio of mononitrile to catalyst is at least 10 and less than 25.

7. The process of claim 4 wherein the molar ratio of mononitrile to catalyst is between 10 and 20.

8. The process of claim 4 wherein the molar ratio of mononitrile to catalyst is between 15 and 20.

9. The process of claim 1, further comprising contacting 1,1,1,3,3-pentachloro-4,4,4-trifluorobutane with HF in the gas or liquid phase, with hydrogen fluoride in the presence of a fluorination catalyst, form a product comprising 2,2-dichloro-1,1,1,4,4,4-hexafluorobutane.

10. The process of claim 9 wherein the process of contacting 1,1,1,3,3-pentachloro-4,4,4-trifluorobutane with HF is performed in the gas phase.

11. The process of claim 9 wherein the process of contacting 1,1,1,3,3-pentachloro-4,4,4-trifluorobutane with HF is performed in the liquid phase.

12. The process of claim 9, further comprising contacting 2,2-dichloro-1,1,1,4,4,4-hexafluorobutane with base to produce a product mixture comprising 1,1,1,4,4,4-hexafluoro-2-butyne ($CF_3C\equiv CCF_3$).

13. The process of claim 12 wherein the process is performed in the presence of a phase transfer catalyst.

14. The process of claim 13 wherein the phase transfer catalyst includes a quaternary ammonium salt.

15. The method of claim 14, wherein the quaternary ammonium salt includes tetrabutylammonium bromide or N-methyl-N, N, N-trioctylammonium chloride.

16. The method of claim 12, further comprising contacting 1,1,1,4,4,4-hexafluoro-2-butyne with hydrogen at a temperature and pressure sufficient to produce a product mixture comprising Z-1,1,1,4,4,4-hexafluoro-2-butene.

17. The method of claim 9, wherein the hydrogenation catalyst is a palladium catalyst.

18. The method of claim 17, wherein the palladium catalyst is a Lindlar catalyst.

19. The method of claim 17, wherein the palladium catalyst comprises palladium dispersed on aluminum oxide or titanium silicate, doped with silver and/or a lanthanide.

20. The process of claim 2 wherein the halogenated alkane is 1,1,1-trichloro-2,2,2-trifluoroethane and the olefin is vinylidene chloride.

21. The process of claim 2 wherein the halogenated alkane is carbon tetrachloride and the olefin is 2-chloro-3,3,3-trifluoropropene.

22. The process of claim 20, wherein the molar ratio of mononitrile to catalyst is at least 10 and less than 25.

23. The process of claim 21, wherein the molar ratio of mononitrile to catalyst is at least 10 and less than 25.

* * * * *